US011324423B2

(12) United States Patent
Lin

(10) Patent No.: US 11,324,423 B2
(45) Date of Patent: May 10, 2022

(54) NON-INVASIVE SYSTEM FOR TESTING BLOOD SUGAR AND METHOD OF THE SAME

(71) Applicant: eTouch Medical Inc., New Taipei (TW)

(72) Inventor: Jeng-Tay Lin, New Taipei (TW)

(73) Assignee: eTouch Medical Inc., New Taipei (TW)

( * ) Notice: Subject to any disclaimer, the term of this patent is extended or adjusted under 35 U.S.C. 154(b) by 156 days.

(21) Appl. No.: 16/551,809

(22) Filed: Aug. 27, 2019

(65) Prior Publication Data

US 2021/0059581 A1    Mar. 4, 2021

(51) Int. Cl.
*A61B 5/1477* (2006.01)
*A61B 5/145* (2006.01)
*A61B 5/00* (2006.01)

(52) U.S. Cl.
CPC ........ *A61B 5/14532* (2013.01); *A61B 5/1477* (2013.01); *A61B 5/6826* (2013.01); *A61B 5/742* (2013.01)

(58) Field of Classification Search
CPC . A61B 5/14532; A61B 5/1477; A61B 5/6826; A61B 5/742
See application file for complete search history.

(56) References Cited

U.S. PATENT DOCUMENTS

| 4,448,199 A * | 5/1984 | Schmid | A61B 5/02438 |
| | | | 600/393 |
| 5,307,263 A * | 4/1994 | Brown | G01N 33/48792 |
| | | | 600/301 |
| 7,395,104 B2 * | 7/2008 | Mouradian | A61B 5/14532 |
| | | | 600/345 |
| 10,194,871 B2 * | 2/2019 | Newberry | A61B 5/6893 |
| 2017/0238851 A1 * | 8/2017 | Duhamel | A61B 5/14546 |

FOREIGN PATENT DOCUMENTS

JP     4443335 B2 *   3/2010

OTHER PUBLICATIONS

Alexandros Karagiannis. Biomedical Time Series Processing and Analysis Methods: The Case of Empirical Mode Decomposition, Aug. 2011, InTech, p. 61-80 (Year: 2011).*

* cited by examiner

*Primary Examiner* — Patrick Fernandes
*Assistant Examiner* — Liam A Wallace
(74) *Attorney, Agent, or Firm* — Lin & Associates Intellectual Property, Inc.

(57) ABSTRACT

Disclosed is a non-invasive system for testing blood sugar and a method of the same. The system includes a case, a control key unit, an input electrode unit, a signal filter unit, a signal transformation unit, a control processing unit, a signal amplification unit, an output electrode unit, a driver, a display unit, and a battery unit for preliminarily testing and instantly showing blood sugar or glucose in a non-invasive manner. Owing to a simple structure without any additional device or connection wire, the system is easy to use and practical to assist the user to readily test blood sugar. As a result, the present invention effectively avoids any potential risk of infection of bacteria or other microorganism due to frequently sampling the blood by pricking the finger, and particularly provides a function of fast and readily testing blood sugar everywhere for long term monitoring.

4 Claims, 5 Drawing Sheets

| User | Age(Y) | Body Status | Tested LU | Calculated GLU |
|---|---|---|---|---|
| A | 28 | Empty /After-meal | 91/83 | 86/104 |
| B | 29 | Empty /After-meal | 90/108 | 91/105 |
| C | 59 | Empty /After-meal | 111/193 | 115/169 |
| D | 59 | Empty /After-meal | 120/154 | 122/145 |

FIG. 5

NON-INVASIVE SYSTEM FOR TESTING BLOOD SUGAR AND METHOD OF THE SAME

BACKGROUND OF THE INVENTION

1. Field of the Invention

The present invention relates to a non-invasive system for testing blood sugar and a method of the same, and more specifically to a non-invasive system for testing blood sugar for preliminarily testing and instantly showing blood sugar or glucose of the user in a non-invasive manner to assist the user to test blood sugar by a simple structure without any additional device or connection wire, thereby avoiding any potential risk of infection due to bacteria or other microorganism during sampling the blood by pricking the finger, and particularly fast and readily testing blood sugar everywhere for long term monitoring.

2. The Prior Arts

It has been well known that blood sugar refers to glucose concentration in human blood, and generally, glucose as one of crucial nutrients is generated by digestion of food in small intestines and then fed into blood. Glucose is transferred to cells of human body to serve as the primary energy substance. Thus, blood sugar is one of key indicators for physical status, and strongly related to cell metabolism and activity. Normally, blood sugar is controlled within a very narrow range like 800-1200 mg/L.

Dysfunction of blood sugar high or low blood sugar may cause some diseases. For example, continuous high blood sugar results in diabetes, and is one of the most common diseases. For low blood sugar, patient may feel dizzy, lose focus, or even get shock.

For the diabetic, it is necessary to keep watch on blood sugar, and ready to inject insulin to reduce blood sugar to a normal value so as to prevent crucial organs of the body from damage due to high blood sugar.

Traditionally, blood sugar is tested by pricking one finger via a needle to sample fresh blood, and then mixing the sampled blood with some agent to check color change, or directly examined by one specific instrument or device. Apparently, the wound of the finger caused by the needle suffers from infection of bacteria, and human immunity is possibly deteriorated if the finger is pricked too often. In addition, the wound may heal over slowly.

Therefore, it is greatly needed to provide a non-invasive system for testing blood sugar and a method of the same for preliminarily testing and instantly showing blood sugar or glucose of the user in a non-invasive manner, thereby overcoming the problems in the prior arts.

SUMMARY OF THE INVENTION

The primary objective of the present invention is to provide a non-invasive system comprising a case, a control key unit, an input electrode unit, a signal filter unit, a signal transformation unit, a control processing unit, a signal amplification unit, an output electrode unit, a driver, a display unit, and a battery unit for preliminarily testing and instantly showing blood sugar or glucose (GLU) of a user in a non-invasive manner.

Specifically, the case is configured to be electrical insulation and water-proof, and provided with an accommodating space, and the control key unit allows the user to control electrical operation of the non-invasive system.

Additionally, the input electrode unit comprises at least two input electrodes made of conductive material with a thin sheet shape for contacting the user and generating an analog input signal. The signal filter unit is electrically connected to the at least two input electrodes for receiving the input signal, and generating and transferring a filtered signal through a filter process. The signal transformation unit is electrically connected to the signal filter unit for receiving the filtered signal, and generating and transferring a digital converted signal through an analog-to-digital conversion.

Further, the control processing unit is electrically connected to the signal transformation unit for receiving the converted signal, generating and transferring a blood sugar information through a blood sugar calculation process. The control processing unit also performs an active trigger operation to generate and transfer a trigger signal as a square wave with a frequency of 100 to 500 Hz.

The signal amplification unit is electrically connected to the control processing unit for receiving the trigger signal, and generating and transferring a trigger amplified signal. The output electrode unit comprises at least two output electrodes made of conductive material with a thin sheet shape. The at least two output electrodes are electrically connected to the signal amplification unit for contacting the user to receive the trigger amplified signal, and generate and transfer a trigger driving signal to the user. In particular, the input signal of the at least two input electrodes is configured to correspond to the trigger driving signal.

The above driver is electrically connected to the control processing unit for receiving the blood sugar information, and generating and transferring a display driving signal, and the display unit is electrically connected to the driver for receiving and displaying the display driving signal. Further, the battery unit comprises at least one battery for supplying power to the control processing unit and the display unit for operation.

Moreover, the accommodating space of the case accommodates the control key unit, the input electrode unit, the signal filter unit, the signal transformation unit, the control processing unit, the signal amplification unit, the output electrode unit, the driver, the display unit, and the battery unit, and the control key unit, the input electrode unit, the output electrode unit, and the display unit are partly exposed on a upper surface or a lower surface of the case. Particularly, the signal filter unit, the signal transformation unit, the control processing unit, the signal amplification unit, the driver, and the battery unit are enclosed and insulated by the case for protection.

Also, the control processing unit is electrically connected to the control key unit for the user to select an operation mode through the control key unit.

Another objective of the present invention is to provide a method of testing blood sugar or glucose (GLU) of a user in a non-invasive manner comprising steps S1, S10, S20, S30, S40, S50, S60, and S70. The method is implemented by using a control processing unit in collocation with a case, a control key unit, an input electrode unit, a signal filter unit, a signal transformation unit, a signal amplification unit, an output electrode unit, a driver, a display unit, and a battery unit. Also, the control key unit, the input electrode unit, the signal filter unit, the signal transformation unit, the control processing unit, the signal amplification unit, the output electrode unit, the driver, the display unit, and the battery unit are accommodated in the case for protection.

In step S1, the method starts and waits for a standby period of time after the input electrode unit is contacted, and in step S10, the input signal is sampled from the at least two input electrodes. In step S20, an average background signal is calculated by arithmetically averaging 8-20 successive samples of the input signal. In step S30, check whether the average background signal is larger than a noise threshold, and the noise threshold is a real number preset within 300-500. If the average background signal is larger than a noise threshold, then return back to the step S20. If the average background signal is not larger than a noise threshold, then the average background signal is recognized as an effective sensing signal.

In step S40, the effective sensing signal is divided into a first finger signal and a second finger signal. The first finger signal comes from the first input electrode or the second input electrode in contact with a first finger of the user, the second finger signal comes from the first input electrode or the second input electrode in contact with a second finger of the user. Specifically, the first finger is a thumb or a forefinger of a right hand and the second finger is a thumb or a forefinger of a left hand, or alternatively, the first finger is the thumb or the forefinger of the left hand and the second finger is the thumb or the forefinger of the right hand.

In S50, a first finger feedback signal is calculated from the first finger signal. Specifically, the first finger feedback signal is $A1\_ratio$, $A1\_ratio = P1*A1\_m\_ave + P2$, P1 is a first parameter, P2 is a second parameter, P1 is a real number preset within 0.05-0.08, p2 is a real number preset within 21.05-35.34, $A1\_m\_ave$ is an average of $A1\_m$ comprising $A1\_ave$ not larger than a value preset as 600-1500, $A1\_m\_ave$ is considered as a stable feedback signal out of an extreme range, $A1\_ave$ is an arithmetic average of 10 successive samples of the first finger signal, and 100 samples of $A1\_ave$ are calculated. In step S60, a second finger feedback signal is calculated from the second finger signal. Specifically, the second finger feedback signal is $A2\_m\_ave$, $A2\_m\_ave$ is an average of $A2\_m$ comprising $A2\_ave$ not larger than a value preset as 1200-1800, $A2\_m\_ave$ is considered as a stable feedback signal out of a preset extreme range, $A2\_ave$ is an arithmetic average of 10 successive samples of the second finger signal, and 100 samples of $A2\_ave$ are calculated.

In step S70, GLU of the user is calculated from the first finger feedback signal and the second finger feedback signal. Specifically, GLU of the user is contained in the blood sugar information, $GLU = P3*(A2\_m\_ave/P4) - P5)*(((P6 - A1\_ratio)/10.238) - P5)*P7$, P3 is a third parameter, P4 is a fourth parameter, P5 is a fifth parameter, P6 is a sixth parameter, P7 is a seventh parameter, P3 is a real number preset as 1 for the normal mode, within 1.1-1.2 for the diabetes pre-stage mode, and within 1.8-2.2 for the diabetes post-stage mode, P4 is a real number preset within 210-220 for the empty mode and within 200-210 for the after-meal mode, P5 is a real number preset within 0.03-0.06, P6 is a real number preset within 60-70 for the empty mode and within 71-80 for the after-meal mode, and P7 is a percentage preset within ±3%-15%.

Therefore, the present invention provide the non-invasive system for testing blood sugar and the method of the same for preliminarily testing and instantly showing blood sugar or glucose of the user in a non-invasive manner to assist the user to test blood sugar by a simple structure without any additional device or connection wire, thereby avoiding any potential risk of infection due to bacteria or other microorganism during sampling the blood by pricking the finger, and particularly fast and readily testing blood sugar everywhere for long term monitoring.

BRIEF DESCRIPTION OF THE DRAWINGS

The present invention will be apparent to those skilled in the art by reading the following detailed description of a preferred embodiment thereof, with reference to the attached drawings, in which:

FIG. 5 is a comparison for GLU data acquired from the traditional pricking method and thee non-invasive method of the present invention.

DETAILED DESCRIPTION OF THE PREFERRED EMBODIMENT

The accompanying drawings are included to provide a further understanding of the invention, and are incorporated in and constitute a part of this specification. The drawings illustrate embodiments of the invention and, together with the description, serve to explain the principles of the invention.

Figure 1:
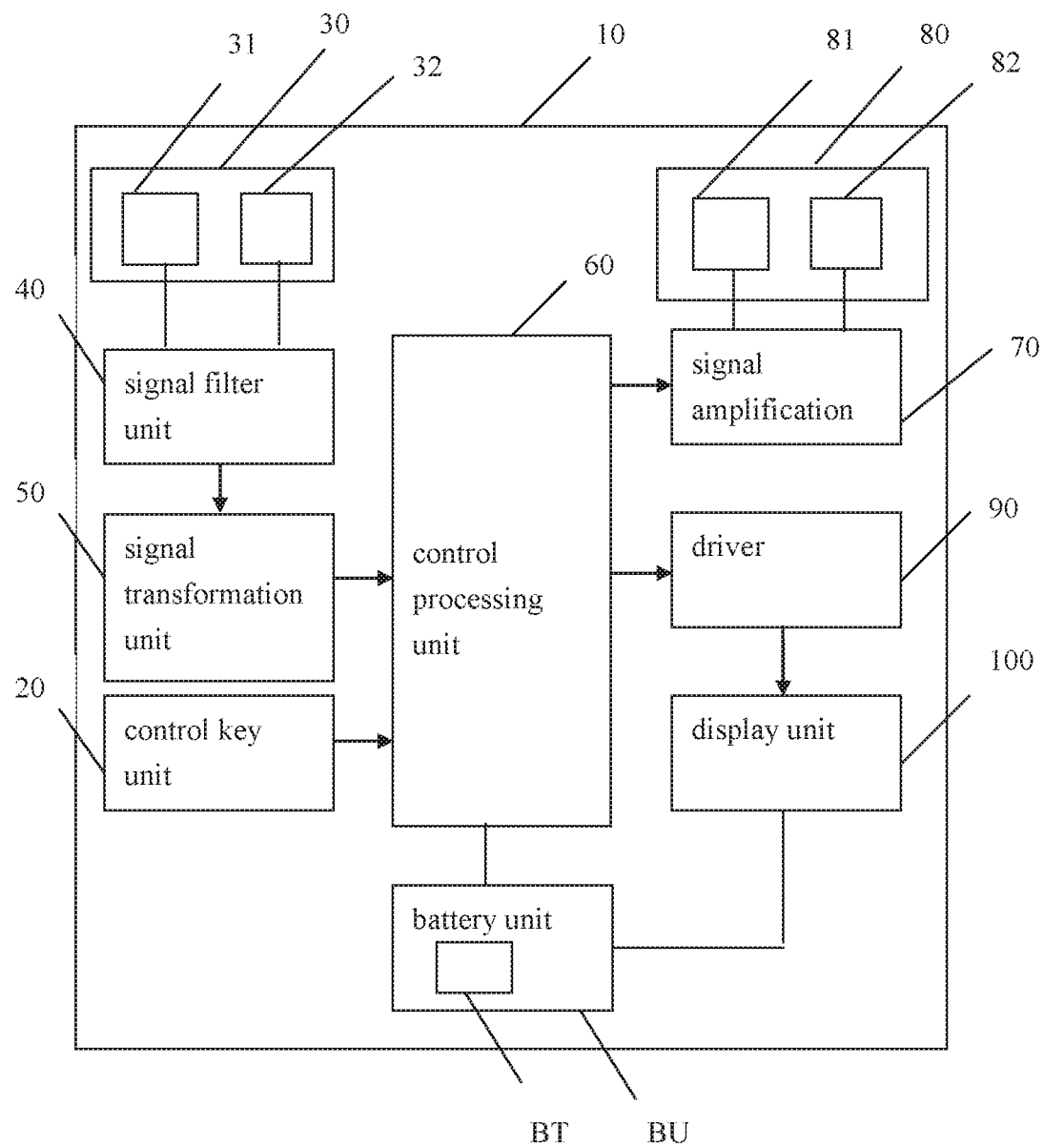
FIG. 1 is a view showing the non-invasive system for testing blood sugar according to the first embodiment of the present invention.
Figure 2:
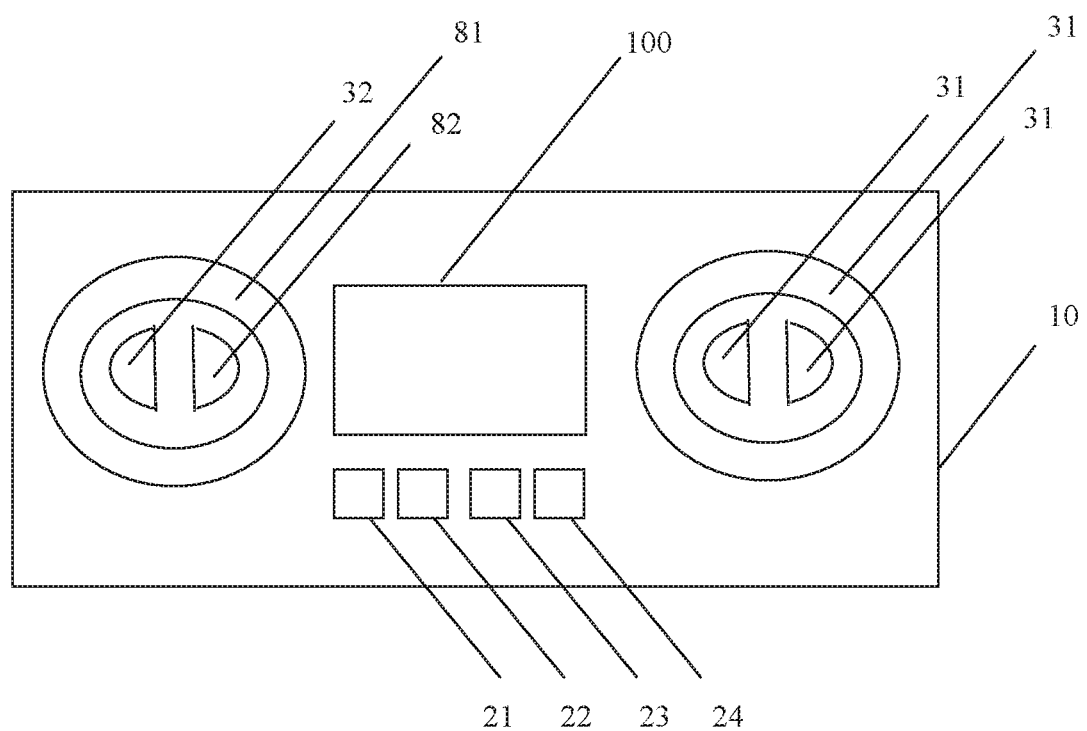
FIG. 2 is a top view of the non-invasive system according to the first embodiment of the present invention.
Figure 3:
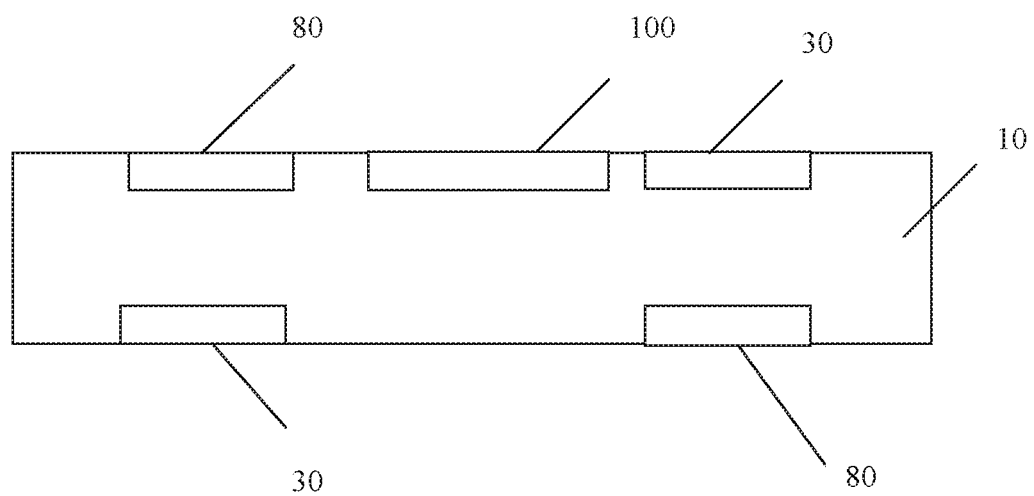
FIG. 3 is a side view of the non-invasive system according to the first embodiment of the present invention.

Please refer to FIGS. 1, 2 and 3. Specifically, FIG. 1 illustrates the non-invasive system for testing blood sugar according to the first embodiment of the present invention, FIG. 2 is a top view of the non-invasive system, and FIG. 3 is a side view of the non-invasive system. As shown in FIGS. 1, 2 and 3, the non-invasive system for testing blood sugar according to the present invention comprises a case 10, a control key unit 20, an input electrode unit 30, a signal filter unit 40, a signal transformation unit 50, a control processing unit 60, a signal amplification unit 70, an output electrode unit 80, a driver 90, a display unit 100, and a battery unit BU for preliminarily testing and instantly showing blood sugar or glucose (GLU) of a user in a non-invasive manner.

Specifically, the case 10 is configured to be electrical insulation and water-proof, and provided with an accommodating space for accommodating the control key unit 20, the input electrode unit 30, the signal filter unit 40, the signal transformation unit 50, the control processing unit 60, the signal amplification unit 70, the output electrode unit 80, the driver 90, the display unit 100, and the battery unit BU. The control key unit 20, the input electrode unit 30, the output electrode unit 80, and the display unit 100 are partly exposed on a upper surface or a lower surface of the case 10, and particularly, the control key unit 20, the signal filter unit 40, the signal transformation unit 50, the control processing unit 60, the signal amplification unit 70, the driver 90, the display unit 100, and the battery unit BU are enclosed and insulated by the case 10 for protection.

In addition, the control key unit 20 allows the user to control electrical operation of the non-invasive system of the present invention. The input electrode unit 30 comprises at least two input electrodes like the first input electrode 31 and the second input electrode 32, which are made of conductive material with a thin sheet shape for contacting the user and generating an analog input signal. The signal filter unit 40 is electrically connected to the input electrode unit 30 for receiving the input signal, and generating and transferring a filtered signal through a filter process using a signal filter, and the signal transformation unit 50 comprises a signal transformer electrically connected to the signal filter unit 40 for receiving the filtered signal, and generating and transferring a digital converted signal through an analog-to-digital conversion (ADC).

Further, the control processing unit 60 comprises a control processor electrically connected to the signal transformation unit 50 for receiving the converted signal, generating and transferring blood sugar information through a blood sugar calculation process. Also, the control processing unit 60 performs an active trigger operation to generate and transfer a trigger signal, which is substantially a square wave with a frequency of 100 to 500 Hz.

The signal amplification unit 70 comprises a signal amplifier electrically connected to the control processing unit 60 for receiving the trigger signal, and generating and transferring a trigger amplified signal. The output electrode unit 80 comprises at least two output electrodes like a first output electrode 81 and a second output electrode 82, which are made of conductive material with a thin sheet shape, and electrically connected to the signal amplification unit 70 for contacting the user, receiving the trigger amplified signal, and generating and transferring a trigger driving signal to the user. In particular, the input signal of the input electrode 30 is configured to correspond to the trigger driving signal.

The driver 90 is a display driver electrically connected to the control processing unit 60 for receiving the blood sugar information, and generating and transferring a display driving signal, and the display unit 100 is electrically connected to the driver 90 for receiving and displaying the display driving signal to illustrate the blood sugar information. Further, the battery unit BU comprises at least one battery BT for supplying power to the control processing unit 60 and the display unit 100 for operation.

Furthermore, the control processing unit 60 is electrically connected to the control key unit 20 for the user to select an operation mode through the control key unit 20.

The above control key unit 20 comprises at least one of a power key 21, an upward move key 22, a downward move key 23, and a confirm key 24. Specifically, the power key 21 is for switching on or switching off the battery unit BU to deliver power or stop supplying power, the upward move key 22 and the downward move key 23 are for upward or downward selecting the operation mode, and the confirm key 24 is configured for the user to confirm the operation mode selected. The operation mode comprises an empty (empty stomach) mode, an after-meal mode, a normal mode, a diabetes pre-stage mode, and a diabetes post-stage mode.

Additionally, the first output electrode 81 of the output electrode unit 80 has a hollow ring part, and the second output electrode 82 has a semilunar part, which is accommodated in the hollow ring part of the first output electrode 81. Similarly, the first input electrode 31 of the input electrode unit 30 has a semilunar part, which is accommodated in the hollow ring part of the first output electrode 81 and does not contact the second input electrode 32. The second input electrode 32 has a hollow ring part, a right semilunar part, and a left semilunar part, and the right semilunar part and the left semilunar part are accommodated in the hollow ring part of the second input electrode 32.

Further, each of the hollow ring part of the first output electrode 31 and the hollow ring part of the second input electrode 32 has a lateral size equal to or larger than a contact area of one finger of the user in contact with the input electrode unit 30 or the output electrode unit 80.

As shown in FIG. 3, the input electrode unit 30 and the output electrode unit 80 are preferably provided on the upper surface or lower surface of the case 10. For example, the user holds the system of the present invention on the upper surface or lower surface with the thumbs and forefingers of the right and left hands such that the user touches and contacts the input electrode unit 30 and the output electrode unit 80 at the same time.

Thus, the non-invasive system according to the first embodiment of the present invention is easy to use, and the user just touches the input electrode unit 30 and the output electrode unit 80 with fingers to invoke the control processing unit 60 to actively test blood sugar in a non-invasive manner, and instantly show the calculated value for blood sugar. In addition, the system of the present invention is simple in the whole structure, and substantially a handheld box without any other device or connection wire so as to greatly improve convenience in use.

Figure 4:
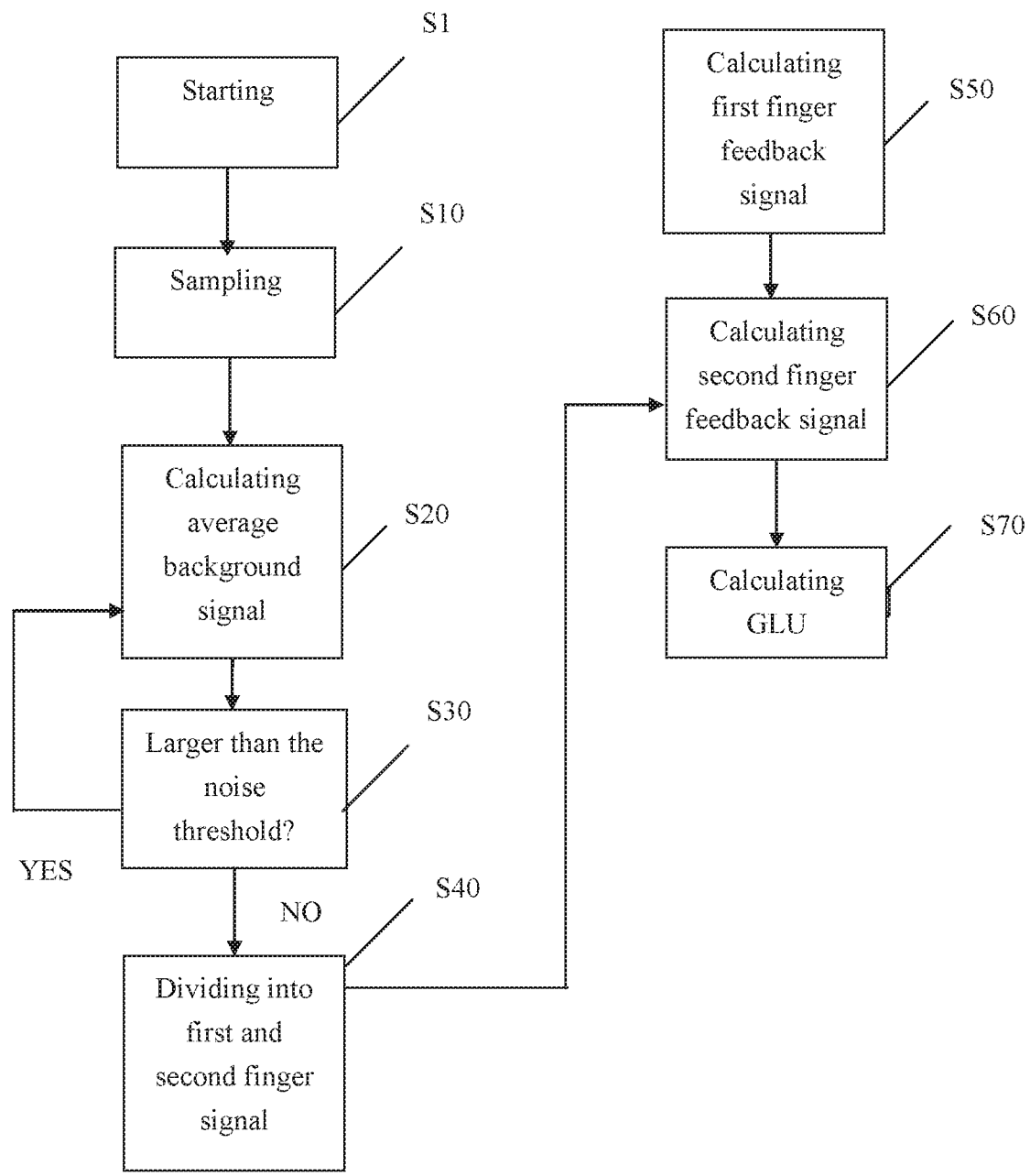
FIG. 4 is a flowchart of the method of testing blood sugar or glucose according to the second embodiment of the present invention.

Please further refer to FIG. 4 illustrating a flowchart of the method of testing blood sugar or glucose according to the second embodiment of the present invention. As shown in FIG. 4, the method of testing blood sugar or glucose generally comprises steps S1, S10, S20, S30, S40, S50, S60, and S70 for testing blood sugar or glucose (GLU) of the user in a non-invasive manner. Specifically, the method of testing blood sugar or glucose is implemented by using a control processing unit in collocation with a case, a control key unit, an input electrode unit, a signal filter unit, a signal transformation unit, a signal amplification unit, an output electrode unit, a driver, a display unit, and a battery unit, the control key unit.

It should be noted that the features of the case, the control key unit, the input electrode unit, the signal filter unit, the signal transformation unit, the control processing unit, the signal amplification unit, the output electrode unit, the driver, the display unit, and the battery unit are similar to the first embodiment, and detailed description is thus omitted.

In step S1, the method of the present invention starts after the input electrode unit is touched or contacted. The control processing unit performs an active trigger operation to generate and transfer a trigger signal as a square wave with a frequency of 100 to 500 Hz. The trigger signal is then transmitted to the user through the signal amplification unit and the output electrode unit, and the input electrode unit generates the analog input signal corresponding to the trigger driving signal. More specifically, the input signal is transferred through the signal filter unit and the signal transformation unit to the control processing unit. Then, the control processing unit waits for a standby period of time, which is preferably 0.6-1.2 seconds.

Next, the step S10 is executed, and the input signal is sampled from the at least two input electrodes. For example, one sample of the input signal is taken at least one period of the trigger signal generated by the control processing unit, and preferably, one sample of the input signal for one period of the trigger signal. Then, in the step S20, an average background signal is calculated by arithmetically averaging 8-20 successive samples of the input signal, and in step S30, check whether the average background signal is larger than a noise threshold, and the noise threshold is a real number preset within 300-500. If the average background signal is larger than a noise threshold, then return back to the step S20. If the average background signal is not larger than a noise threshold, then the average background signal is recognized as an effective sensing signal, and the step S40 is executed.

In step S40, the effective sensing signal is divided into a first finger signal and a second finger signal. The first finger signal comes from the first input electrode or the second input electrode in contact with a first finger of the user, the second finger signal comes from the first input electrode or the second input electrode in contact with a second finger of the user. Specifically, the first finger is a thumb or a forefinger of a right hand and the second finger is a thumb or a forefinger of a left hand, or alternatively, the first finger is the thumb or the forefinger of the left hand and the second finger is the thumb or the forefinger of the right hand.

In S50, a first finger feedback signal is calculated from the first finger signal. Specifically, the first finger feedback signal is A1_ratio, A1_ratio=P1*A1_m_ave+P2, P1 is a first parameter, P2 is a second parameter, P1 is a real number preset within 0.05-0.08, p2 is a real number preset within 21.05-35.34, A1_m_ave is an average of A1_m comprising A1_ave not larger than a value preset as 600-1500, A1_m_ave is considered as a stable feedback signal out of an extreme range, A1_ave is an arithmetic average of 10 successive samples of the first finger signal, and 100 samples of A1_ave are calculated. In step S60, a second finger feedback signal is calculated from the second finger signal. Specifically, the second finger feedback signal is A2_m_ave, A2_m_ave is an average of A2_m comprising A2_ave not larger than a value preset as 1200-1800, A2_m_ave is considered as a stable feedback signal out of a preset extreme range, A2_ave is an arithmetic average of 10 successive samples of the second finger signal, and 100 samples of A2_ave are calculated.

In step S70, GLU of the user is calculated from the first finger feedback signal and the second finger feedback signal. Specifically, GLU of the user is contained in the blood sugar information, GLU=P3*(A2_m_ave/P4)−P5)*(((P6−A1 ratio)/10.238)−P5)*P7, P3 is a third parameter, P4 is a fourth parameter, P5 is a fifth parameter, P6 is a sixth parameter, P7 is a seventh parameter, P3 is a real number preset as 1 for the normal mode, within 1.1-1.2 for the diabetes pre-stage mode, and within 1.8-2.2 for the diabetes post-stage mode, P4 is a real number preset within 210-220 for the empty mode and within 200-210 for the after-meal mode, P5 is a real number preset within 0.03-0.06, P6 is a real number preset within 60-70 for the empty mode and within 71-80 for the after-meal mode, and P7 is a percentage preset within ±3%-15%.

In other words, the method of testing and showing blood sugar or glucose according to the second embodiment of the present invention employs the feedback signal corresponding to the trigger signal to calculate a precise blood sugar value.

To further compare GLU data acquired from the pricking method in the prior arts and the non-invasive method of the present invention, refer to FIG. 5 illustrating four persons with different ages in two modes, including the empty mode and the after-meal mode. It is obvious that the method of the present invention obtains the considerably precise value of blood sugar in comparison with the value obtained by pricking, and in particular, the error is within −12.4% to +12.8%. Therefore, the present invention is indeed practical and helpful for the user or patient to test blood sugar by herself or himself without pricking the finger too often so as to effectively avoid infection caused by bacteria, particularly, implementing fast test and continuously monitoring for a long term period of time.

Although the present invention has been described with reference to the preferred embodiments thereof, it is apparent to those skilled in the art that a variety of modifications and changes may be made without departing from the scope of the present invention which is intended to be defined by the appended claims.

What is claimed is:

1. A non-invasive system for preliminarily testing and showing blood sugar or glucose of a user in a non-invasive manner, comprising:

a case configured to be electrical insulation and waterproof, and provided with an accommodating space;

at least one control key including at least one of an upward move key, a downward move key and a confirm key, wherein the upward move key and the downward move key are for upward or downward selecting one of operation modes, the confirm key is configured for the user to confirm the operation mode selected, and the operation modes include an empty mode, an after-meal mode, a normal mode, a diabetes pre-stage mode, and a diabetes post-stage mode;

at least two input electrodes made of conductive material with a thin sheet shape for contacting the user and generating an analog input signal, the at least two input electrodes including a first input electrode and a second input electrode;

a signal filter electrically connected to the at least two input electrodes for receiving the analog input signal, and generating and transferring a filtered signal through a filter process;

a signal transformer electrically connected to the signal filter for receiving the filtered signal, and generating and transferring a digital converted signal through an analog-to-digital conversion (ADC);

a control processor electrically connected to the signal transformer for receiving the digital converted signal, generating and transferring blood sugar information through a blood sugar calculation process, and performing an active trigger operation to generate and transfer a trigger signal as a square wave with a frequency of 100 to 500 Hz;

a signal amplifier electrically connected to the control processor for receiving the trigger signal, and generating and transferring a trigger amplified signal;

at least two output electrodes made of conductive material with a thin sheet shape electrically connected to the signal amplifier for contacting the user, receiving the trigger amplified signal, and generating and transferring a trigger driving signal to the user, the analog input signal of the at least two input electrodes configured to correspond to the trigger driving signal;

a display driver electrically connected to the control processor for receiving the blood sugar information, and generating and transferring a display driving signal;

a display electrically connected to the display driver for receiving and displaying the display driving signal; and at least one battery for supplying power to the control processor and the display for operation, wherein the control processor performs:

a step S1 for starting and waiting for a standby period of time after the at least two input electrodes are contacted;

a step S10 for sampling the analog input signal from the at least two input electrodes;

a step S20 for calculating an average background signal by arithmetically averaging 8-20 successive samples of the analog input signal;

a step S30 for checking whether the average background signal is larger than a noise threshold, the noise threshold being a real number preset within 300-500, wherein if the average background signal is larger than the noise threshold, then return back to the step S20, and if the average background signal is not larger than the noise threshold, then the average background signal is recognized as an effective sensing signal;

a step S40 for dividing the effective sensing signal into a first finger signal and a second finger signal, wherein the first finger signal comes from the first input electrode or the second input electrode in contact with a first finger of the user, the second finger signal comes from the first input electrode or the second input electrode in contact with a second finger of the user, and the first finger is a thumb or a forefinger of a right hand and the second finger is a thumb or a forefinger of a left hand, or alternatively, the first finger is the thumb or the forefinger of the left hand and the second finger is the thumb or the forefinger of the right hand;

a step S50 for calculating a first finger feedback signal from the first finger signal, a step S60 for calculating a second finger feedback signal from the second finger signal;

and a step S70 for calculating GLU of the user from the first finger feedback signal and the second finger feedback signal.

2. The system as claimed in claim 1, wherein the at least one control key further comprises a power key for switching on or switching off the at least one battery to deliver power or stop supplying power.

3. The system as claimed in claim 1, wherein the at least two output electrodes comprises a first output electrode and a second output electrode, the first output electrode has a hollow ring part, the second output electrode has a semilunar part accommodated in the hollow ring part of the first output electrode, the first input electrode has a semilunar part accommodated in the hollow ring part of the first output electrode and does not contact the second input electrode, the second input electrode has a hollow ring part, a right semilunar part, and a left semilunar part, the right semilunar part and the left semilunar part are accommodated in the hollow ring part of the second input electrode, and each of the hollow ring part of the first output electrode and the hollow ring part of the second input electrode has a lateral size equal to or larger than a contact area of a finger of the user in contact with the at least two input electrodes or the at least two output electrodes.

4. The method as claimed in claim 1, wherein the standby period of time is 0.6-1.2 seconds.

* * * * *